US009227952B2

(12) United States Patent
Phadke

(10) Patent No.: US 9,227,952 B2
(45) Date of Patent: Jan. 5, 2016

(54) SOVAPREVIR POLYMORPHS AND METHODS OF MANUFACTURE THEREOF

(71) Applicant: Achillion Pharmaceuticals, Inc., New Haven, CT (US)

(72) Inventor: Avinash Phadke, Branford, CT (US)

(73) Assignee: Achillion Pharmaceuticals, Inc., New Haven, CT (US)

(*) Notice: Subject to any disclaimer, the term of this patent is extended or adjusted under 35 U.S.C. 154(b) by 0 days.

(21) Appl. No.: 14/211,948

(22) Filed: Mar. 14, 2014

(65) Prior Publication Data

US 2014/0275163 A1 Sep. 18, 2014

Related U.S. Application Data

(60) Provisional application No. 61/786,927, filed on Mar. 15, 2013.

(51) Int. Cl.
*C07D 401/12* (2006.01)

(52) U.S. Cl.
CPC .................................. *C07D 401/12* (2013.01)

(58) Field of Classification Search
None
See application file for complete search history.

(56) References Cited

U.S. PATENT DOCUMENTS

| 6,872,805 | B2 | 3/2005 | Campbell et al. |
| 6,908,901 | B2 | 6/2005 | Bailey et al. |
| 6,995,174 | B2 | 2/2006 | Wang et al. |
| 7,041,698 | B2 | 5/2006 | Ripka et al. |
| 7,176,208 | B2 | 2/2007 | Nakajima et al. |
| 2004/0002448 | A1 | 1/2004 | Tsantrizos et al. |
| 2004/0048802 | A1 | 3/2004 | Ripka et al. |
| 2004/0077551 | A1 | 4/2004 | Campbell et al. |
| 2004/0224900 | A1 | 11/2004 | Bailey et al. |
| 2006/0007708 | A1 | 1/2006 | Lee |
| 2006/0019905 | A1 | 1/2006 | Bailey et al. |
| 2006/0046965 | A1 | 3/2006 | Bailey et al. |
| 2006/0199773 | A1 | 9/2006 | Sausker et al. |
| 2007/0010455 | A1 | 1/2007 | Hewawasam et al. |
| 2007/0093414 | A1 | 4/2007 | Carini et al. |
| 2007/0099825 | A1 | 5/2007 | D'Andrea et al. |
| 2010/0216725 | A1 | 8/2010 | Phadke et al. |
| 2015/0051199 | A1* | 2/2015 | Woodhead et al. ........ 514/230.5 |

FOREIGN PATENT DOCUMENTS

| WO | 0260926 A2 | 8/2002 |
| WO | 03099274 A1 | 12/2003 |
| WO | 03099316 A1 | 12/2003 |
| WO | WO 2004043339 A2 | 5/2004 |
| WO | WO 2004072243 A2 | 8/2004 |
| WO | WO 2004094452 A2 | 11/2004 |
| WO | 2004103996 A1 | 12/2004 |
| WO | 2004113365 A2 | 12/2004 |
| WO | 2005028501 A1 | 3/2005 |
| WO | 2005037214 A2 | 4/2005 |
| WO | WO 2005046712 A1 | 5/2005 |
| WO | WO 2005051410 A1 | 6/2005 |
| WO | WO 2005054430 A2 | 6/2005 |
| WO | 2005073216 A1 | 8/2005 |
| WO | WO 2005070955 A1 | 8/2005 |
| WO | 2005090383 A2 | 9/2005 |
| WO | WO 2005095403 A2 | 10/2005 |
| WO | WO 2006007700 A1 | 1/2006 |
| WO | 2006020276 A2 | 2/2006 |
| WO | WO 2006033878 A1 | 3/2006 |
| WO | WO 2006086381 A2 | 8/2006 |
| WO | WO 2006096652 A2 | 9/2006 |
| WO | 2005007681 A2 | 1/2007 |
| WO | 2007005838 A2 | 1/2007 |
| WO | 2007009109 A2 | 1/2007 |
| WO | 2007009227 A1 | 1/2007 |
| WO | 2007014919 A1 | 2/2007 |
| WO | 2007015824 A2 | 2/2007 |
| WO | 2007030656 A1 | 3/2007 |
| WO | 2007044893 A2 | 4/2007 |
| WO | 2008008502 A1 | 1/2008 |

OTHER PUBLICATIONS

Andrews et al., "Pyrrodlidine-5,5-trans-lactams. 2. The Use of X-ray Crystal Structure Data in the Optimization of P3 and P4 Substituents" Organic Letters, vol. 4, No. 25, (2002), pp. 4479-4482.
Arasappan et al., "Hepatitis C Virus NS3-4A Serine Protease Inhibitors: SAR of P2 Moeity with Improved Potency" Bioorganic and Medicinal Chemistry Letters, 15, (2005), pp. 4180-4184.
Barbato et al., "Inhibitor Binding Induces Active Site Stabilization of the HCV NS3 Protein Serine Protease Domain".
Di Marco et al., "Inhibition of the Heapatitis C Virus NS3/4A Protease" The Journal of Biological Chemistry, vol. 275, No. 10, Issue of Mar. 10, 2000, pp. 7152-7157.
International Search Report of the International Searching Authority for International Application No. PCT/US2007/016018; International Filing Date: Jul. 13, 2007; Date of Mailing: Dec. 12, 2007, 14 pages.
International Search Report of the International Searching Authority for International Patent Application No. PCT/US2014/028348; International Filing Date: Mar. 14, 2014; Date of Mailing: Jun. 11, 2014; 4 Pages.
Liu et al., "Hepatitis C NS3 Protease Inhibition by Peptidyl-a-Ketoamide Inhibitors: Kinetic Mechanism and Structure" Archives of Biochemistry and Biophysics, 421, (2004), pp. 207-216.
Ontoria et al., "The Design and Enzyme-Bound Crystal Structure of Indoline Based Peptidomimetic Inhibitors of Hepatitis C Virus NS3 Protease" Journal of Med. Chem., 47, (2004), pp. 6443-6446.
Slater et al., "Pyrrolidine-5,5-Trans-Lactams. 4. Incorporation of a P3/P4 Urea Leads to Potent Intracellular Inhibitors of Hepatitis C Virus NS3/4A Protease" Organic Letters, vol. 5, No. 24, (2003), pp. 4627-4630.
Venkatraman, et al., Discovery of (1R,5S)-N-[3-Amino-1-(cyclobutylmethyl)-2,3-dioxopropyl]-3-[2(S)-[[[(1, 1-dimethyl-lethyl)amino]carbonyl]amino[-3,3-dimethyl-1-oxobutyl]-6,6-dimethyl-3-azabicyclo[3.1.0]hexan-2(S)-carboxamide (SCH 503034), a Selective, Po.
Written Opinion of the International Searching Authority for International Patent Application No. PCT/US2014/028348; International Filing Date: Mar. 14, 2014; Date of Mailing: Jun. 11, 2014; 5 Pages.
Written Opinion of the International Searching Authority for International Application No. PCT/US2007/016018; International Filing Date: Jul. 13, 2007, Date of Mailing Dec. 12, 2007, 8 Pages.

* cited by examiner

*Primary Examiner* — Thomas S Heard
(74) *Attorney, Agent, or Firm* — Knowles Intellectual Property Strategies, LLC; Brent R. Bellows

(57) ABSTRACT

The disclosure provides crystalline Sovaprevir forms. The crystalline forms of Sovaprevir comprise a Form A polymorph, a Form B polymorph, a Form C polymorph, a Form D polymorph, and a Form E polymorph. The Form A, B, C, D, and E polymorphs exhibit X-ray powder diffraction patterns having peak locations in accordance with FIGS. 1, 4, 7, 10, and 13, respectively.

17 Claims, 15 Drawing Sheets

SOVAPREVIR POLYMORPHS AND METHODS OF MANUFACTURE THEREOF

CROSS REFERENCE TO RELATED APPLICATION

This application claims priority from U.S. Provisional application No. 61/786,927 filed Mar. 15, 2013, which is hereby incorporated by reference in its entirety.

FIELD OF THE INVENTION

Sovaprevir polymorphic crystalline forms and methods of making Sovaprevir polymorphs are disclosed.

DESCRIPTION OF THE RELATED ART

The molecules in a crystalline solid are arranged in a crystal lattice, a three dimensional structure in which structural units (unit cells) are repeated in a regular manner. Different crystal forms of the same substance (polymorphs) have distinct crystal lattices, which can result in important differences in their properties, utilities, and commercial values. For example, graphite and diamond are polymorphs of crystalline carbon. Polymorphs of pharmaceutical compounds can also be distinctly, if not as dramatically, different in their properties, including properties relevant to the development of formulations of such pharmaceutical compounds and to the development of solid dosage forms, such as tablets and capsules, comprising such formulations. The crystal form of a drug may also be relevant to compliance with regulatory requirements concerning its manufacture.

Sovaprevir has been identified as useful for the treatment of chronic HCV infection. To improve therapeutic use of Sovaprevir, identification of new polymorphs of Sovaprevir is desirable. This disclosure meets this need and provides further advantages which are shown herein.

SUMMARY

Disclosed herein are crystalline Sovaprevir forms. Sovaprevir crystalline forms include Form A polymorph, a Form B polymorph, a Form C polymorph, a Form D polymorph, and a Form E polymorph.

Also disclosed is a composition comprising the Sovaprevir disclosed above, wherein at least 90 wt % of the Sovaprevir is the Form A polymorph, the Form B polymorph, the Form C polymorph, the Form D polymorph, the Form E polymorph, or a combination thereof.

Also disclosed is method for treating HCV, the method comprising administering to a patient in need of such treatment a therapeutically effective amount of the pharmaceutical composition.

The above described and other features are exemplified by the following figures and detailed description.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
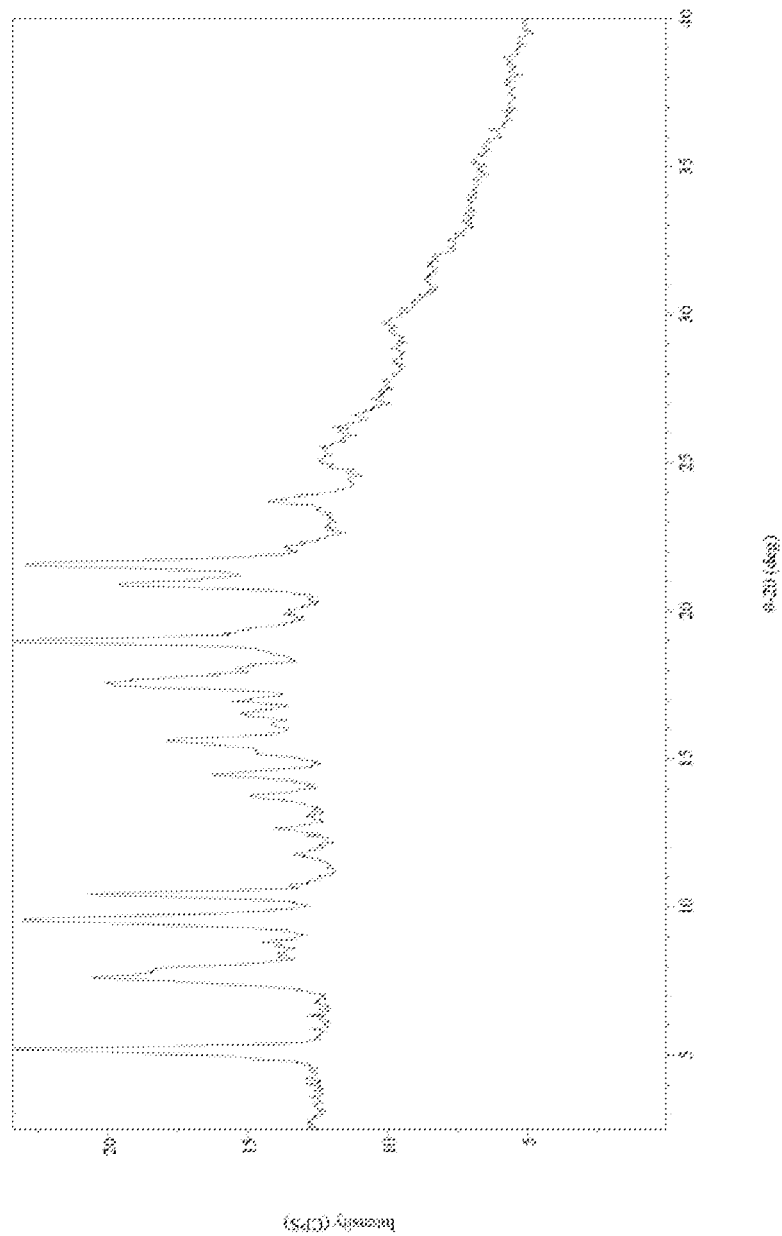
FIG. 1 is a graph of intensity (counts per second, CPS) versus scattering angle (degrees 2θ) showing the results of X-ray powder diffraction analysis of the Form A polymorph of Example 1.

The disclosure now will be described in more detail, with reference to the accompanying figures. This disclosure may, however, be embodied in many different forms, and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

TERMINOLOGY

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, i.e., the Sovaprevir, and at least one other substance, such as a carrier, excipient, or diluent. Pharmaceutical compositions meet the U.S. FDA's GMP (good manufacturing practice) standards for human or non-human drugs.

The term "carrier" applied to pharmaceutical compositions described herein refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing the Sovaprevir with at least one additional active agent" means the Sovaprevir and the additional active agent(s) are provided simultaneously in a single dosage form, provided concomitantly in separate dosage forms, or provided in separate dosage forms for administration separated by some amount of time that is within the time in which both the Sovaprevir and the at least one additional active agent are within the blood stream of a patient. The Sovaprevir and the additional active agent need not be prescribed for a patient by the same medical care worker. The additional active agent or agents need not require a prescription. Administration of the Sovaprevir or the at least one additional active agent can occur via any appropriate route, for example, oral tablets, oral capsules, oral liquids, inhalation, injection, suppositories or topical contact.

"Treatment," as used herein includes providing Sovaprevir and at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of the Sovaprevir and at least one additional active agent to a patient having or susceptible to a hepatitis C infection.

A "therapeutically effective amount" of a pharmaceutical combination of this disclosure means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the limit of quantitation (30 IU/mL, as measured by the Roche TaqMan(R) assay) or more preferably below the limit of detection (10 IU/mL, Roche TaqMan).

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Sovaprevir, i.e., (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide, has the following structure 1.

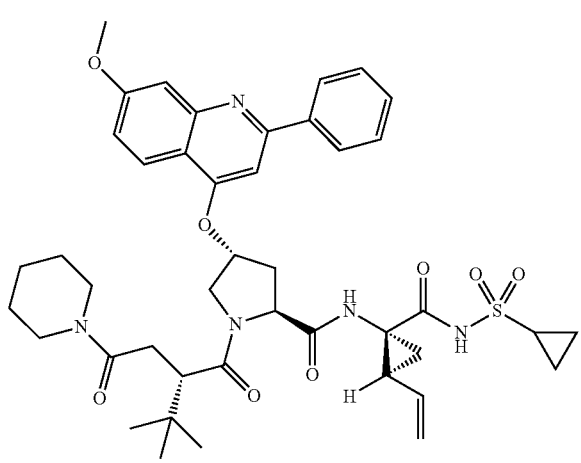

(1)

Various polymorphs of Sovaprevir have been identified. A first polymorph which can result directly from the synthesis of Sovaprevir without further treatment has been designated Form A. A polymorph which can be prepared by slow evaporation of a solution of Sovaprevir in acetonitrile:water 80:20 (v/v) has been designated Form B. A polymorph which can be prepared from an isopropanol slurry at approximately 48° C. has been designated Form C. A second polymorph resulting directly from the synthesis of Sovaprevir without further treatment has been designated Form E.

Disclosed is a crystalline Sovaprevir form having a mass median diameter of no greater than about 100 microns as determined by laser light diffraction wherein the Sovaprevir comprises the Form A polymorph, the Form B polymorph, the Form C polymorph, the Form D polymorph, the Form E polymorph, or a combination thereof.

Polymorph A exhibits an X-ray powder diffraction pattern having the characteristic 2θ values of FIG. 1. Polymorph A is characterized by an X-ray powder diffraction pattern obtained from a Cu Kα source which comprises peaks at 2θ values of 5.1, 9.5, 12.6, 15.7, 17.6, and 21.7+/−0.2; or 7.7, 10.4, 13.8, 16.6, 18.8, and 24.0+/−0.2; or 8.8, 11.7, 14.3, 17.0, and 21.0+/−0.2.

Figure 4:
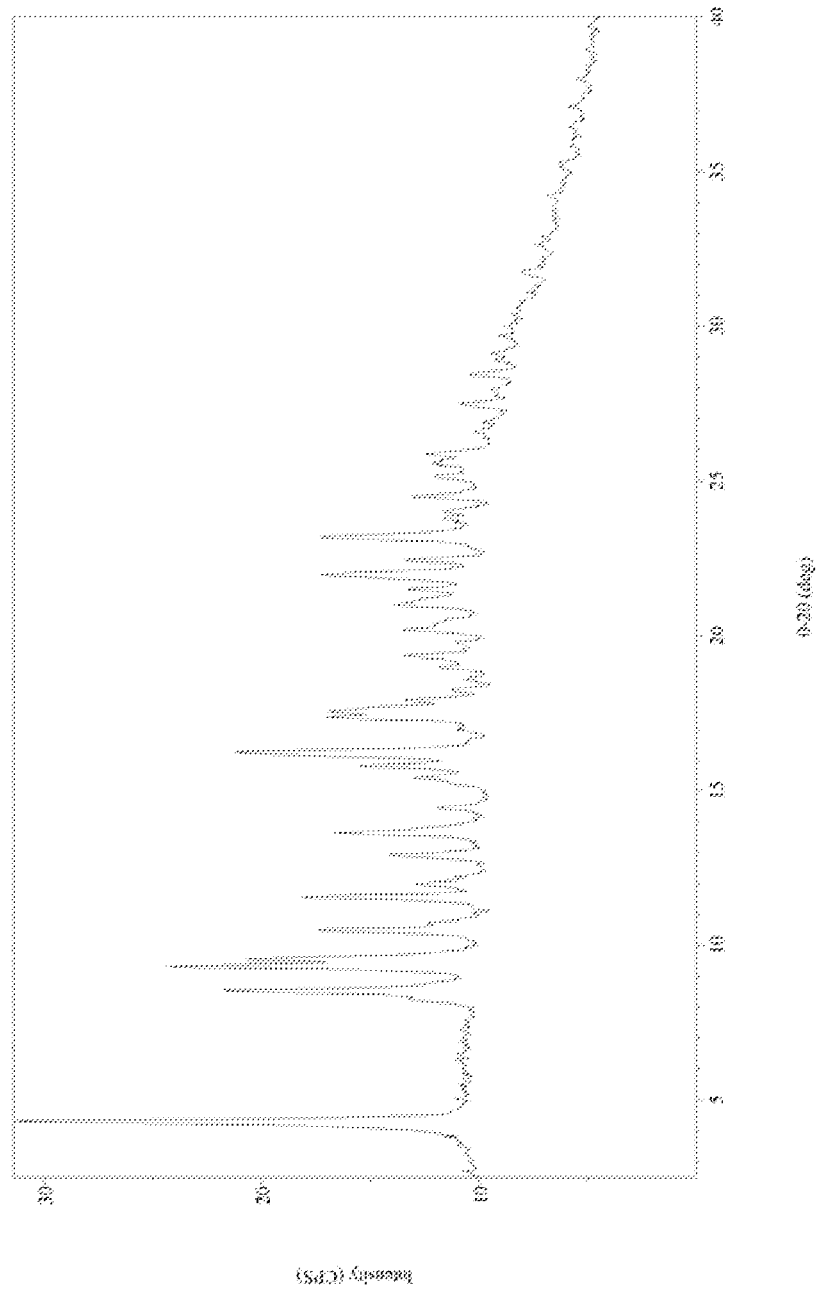
FIG. 4 is a graph of intensity (counts per second, CPS) versus scattering angle (degrees 2θ) showing the results of X-ray powder diffraction analysis of the Form B polymorph of Example 2.

Polymorph B exhibits an X-ray powder diffraction pattern having the characteristic 2θ values of FIG. 4. Polymorph B is characterized by an X-ray powder diffraction pattern obtained from a Cu Kα source which comprises peaks at 2θ values of 4.4, 9.8, 12.3, 15.4, 17.5, 19.5, 21.8, 23.6, 25.5, and 28.7+/−0.2; or 8.7, 10.7, 13.0, 14.9, 17.7, 20.3, 22.3, 23.6, and 25.8+/−0.2; or 9.5, 11.7, 14.5, 16.4, 18.1, 21.2, 22.7, 24.7, and 27.6+/−0.2.

Figure 7:
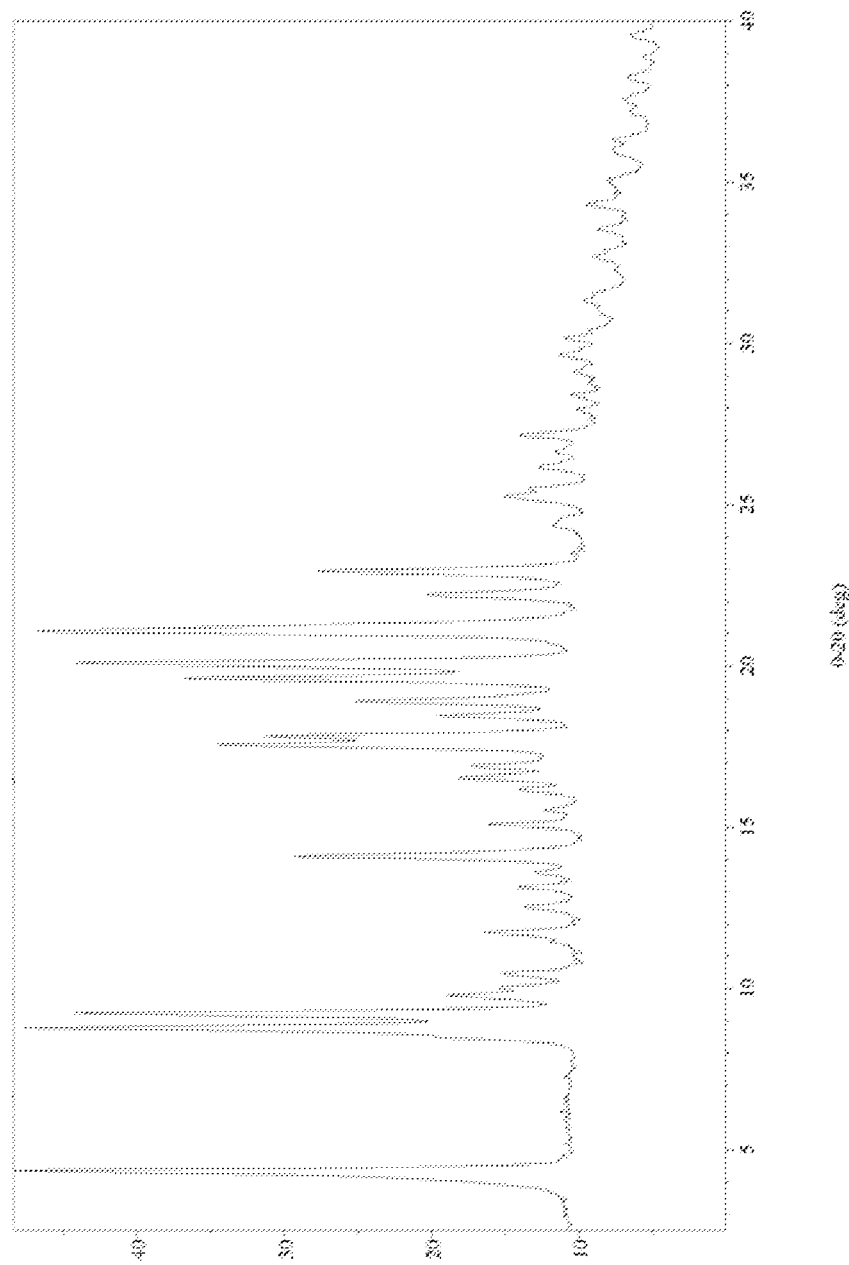
FIG. 7 is a graph of intensity (counts per second, CPS) versus scattering angle (degrees 2θ) showing the results of X-ray powder diffraction analysis of the Form C polymorph of Example 3.

Polymorph C exhibits an X-ray powder diffraction pattern having the characteristic 2θ values of FIG. 7. Polymorph C is characterized by an X-ray powder diffraction pattern obtained from a Cu Kα source which comprises peaks at 2θ values of 4.5, 9.9, 11.8, 14.4, 17.0, 17.7, 19.2, 21.5, and 25.4+/−0.2; or 8.9, 10.1, 12.6, 15.2, 17.7, 18.1, 19.7, 22.5, and 27.4+/−0.2; or 9.4, 10.5, 13.3, 16.3, 17.9, 18.6, 20.4, and 23.3+/−0.2.

Figure 10:
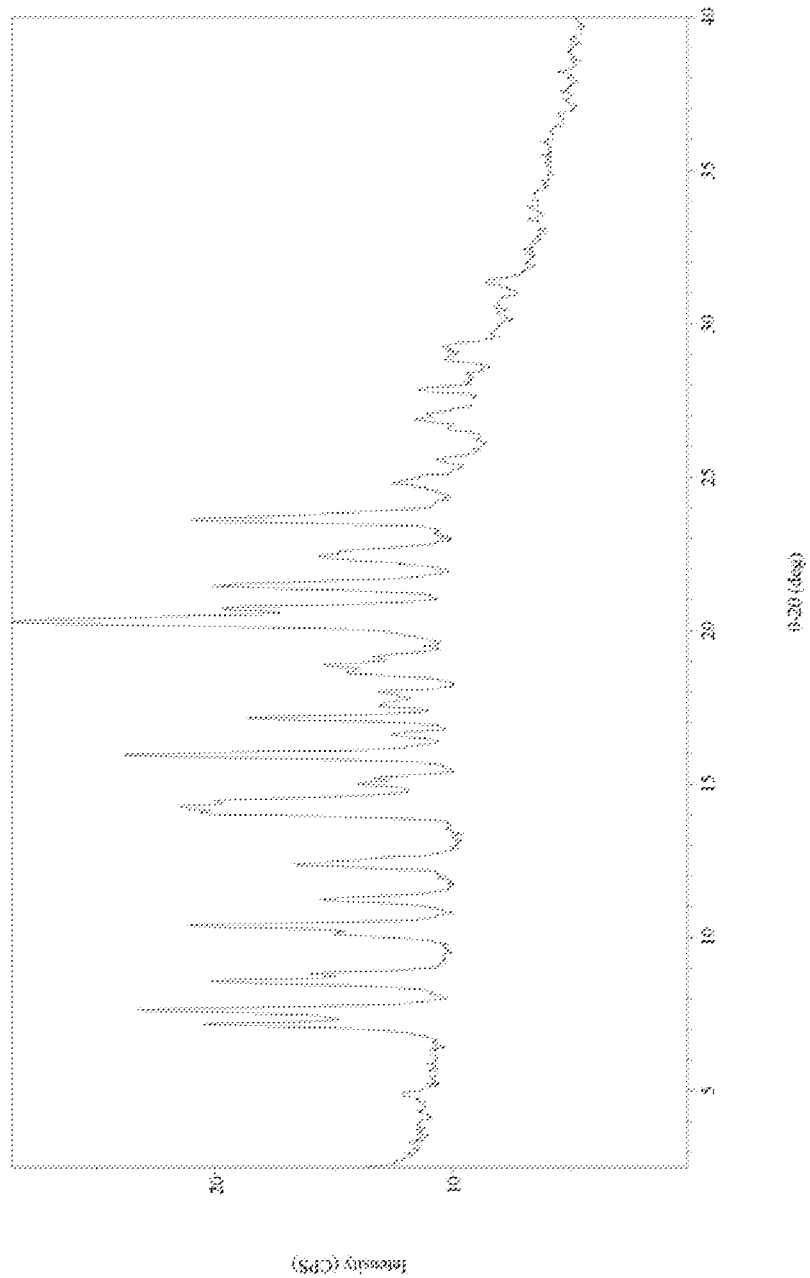
FIG. 10 is a graph of intensity (counts per second, CPS) versus scattering angle (degrees 2θ) showing the results of X-ray powder diffraction analysis of the Form D polymorph of Example 4.

Polymorph D exhibits an X-ray powder diffraction pattern having the characteristic 2θ values of FIG. 10. Polymorph D is characterized by an X-ray powder diffraction pattern obtained from a Cu Kα source which comprises peaks at 2θ values of 7.4, 8.9, 11.4, 15.1, 17.1, 19.1, 20.7, and 24.0+/−0.2; or 7.7, 10.2, 12.6, 16.0, 17.7, 19.2, 21.6, and 25.0+/−0.2; or 8.6, 10.5, 14.5, 16.8, 18.1, 20.5, 22.6, and 27.0+/−0.2.

Figure 13:
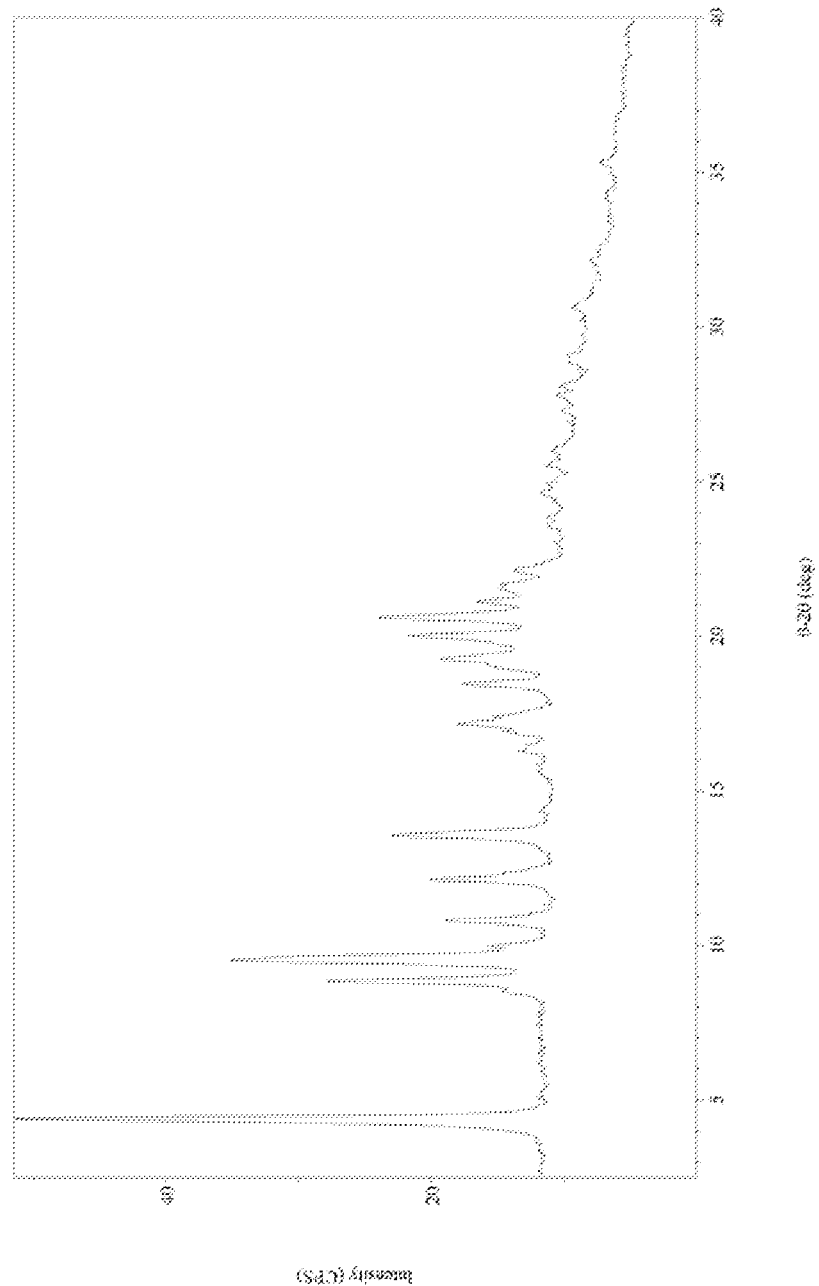
FIG. 13 is a graph of intensity (counts per second, CPS) versus scattering angle (degrees 2θ) showing the results of X-ray powder diffraction analysis of the Form E polymorph.

Polymorph E exhibits an X-ray powder diffraction pattern having the characteristic 2θ values of FIG. 13. Polymorph E is characterized by an X-ray powder diffraction pattern obtained from a Cu Kα source which comprises peaks at 2θ values of 4.5, 10.9, 17.4, 20.2, and 21.7+/−0.2; or 9.0, 12.3, 18.6, 20.7, and 22.2+/−0.2; or 9.7, 13.7, 19.4, and 21.3+/−0.2.

When analyzed by differential scanning calorimetry (DSC), Sovaprevir has a primary endotherm, wherein the primary endotherm is defined as the most endothermic peak observed in a DSC result. The Form A polymorph has a primary endotherm, as determined by DSC, at about 174 to about 183° C., specifically 179° C., the Form B polymorph has a primary endotherm at about 94 to about 104° C., specifically 99° C., the Form C polymorph has a primary endotherm at about 168 to about 177° C., specifically 172° C., the Form D polymorph has a primary endotherm at about 200 to about 210° C., specifically 205° C. and the Form E polymorph has a primary endotherm at about 151 to about 161° C., specifically 156° C.

Sovaprevir has any suitable particle size, and has a mass median diameter of no greater than about 100 micrometers (μm), specifically no greater than about 50 μm. In an embodiment the Sovaprevir has an average particle size, e.g., average largest particle size, of 1 to 100 micrometers (μm), specifically 5 to 50 μm. The particles have any suitable shape, may have a curvilinear or rectilinear shape, and may be spheres, platelets, needles, or a combination thereof. A desirable particle size may be provided by milling, grinding, or sieving, for example.

Representative X-ray powder diffraction (XRPD) patterns for the polymorphs designated Form A, B, C, D, and E are shown in FIGS. 1, 4, 7, 10, and 13, respectively. In an embodiment, the polymorphs have peak locations and/or peak intensities in accordance with these XRPD patterns.

Forms A, B, C, D, and E may each independently comprise about 0.1 to about 10 wt % water, about 0.1 to about 5 wt % water, about 0.1 to about 1 wt % water, specifically about 0.2 to about 0.8 wt % water. In an embodiment, Form A comprises about 0.2 to about 0.8 wt % water, specifically about 0.4 to about 0.6 wt % water. Also, Form D comprises less than about 10 wt % water, specifically less than about 5 wt % water, more specifically about 0.01 to about 10 wt % water, or about 0.1 to about 5 wt % water. Also, Form E may comprise about 0.05 to about 0.55 wt % water, specifically about 0.1 to about 0.5 wt % water. The content of water may be determined by Karl Fischer titration.

The disclosure includes Sovaprevir compositions comprising a crystalline form of Sovaprevir wherein at least 90 wt % of the Sovaprevir is the Form A polymorph, the Form B polymorph, the Form C polymorph, the Form D polymorph, the Form E polymorph, or a combination thereof. The disclosure includes Sovaprevir compositions comprising a crystalline form of Sovaprevir wherein at least 90 wt % of the Sovaprevir is the Form A polymorph, the Form B polymorph, the Form C polymorph, the Form E polymorph, or a combination thereof. The disclosure includes Sovaprevir compositions comprising a crystalline form of Sovaprevir wherein at least 90 wt % of the Sovaprevir is the Form E polymorph, or a combination thereof. In certain embodiments this composition comprises less than about 10 wt % of a Form D polymorph.

The disclosure includes Sovaprevir compositions wherein essentially all of the sovaprevir is the Form A polymorph. The disclosure includes Sovaprevir compositions comprising any of the combinations of polymorph Form A, B, C, D, and E discussed herein or Form A along in combination with a physiologically acceptable carrier or excipient.

In an embodiment the composition may be suitable for pharmaceutical use and may be in the form of a pharmaceutical composition. The pharmaceutical composition has any suitable form, and may be a tablet, capsule, solution, suspension, or a combination thereof.

The pharmaceutical composition may be used to treat a disorder, e.g., HCV. Therapeutic methods provided herein may be used to treat an existing disorder, or to prevent, decrease the severity of, or delay the onset of a disorder in a patient. Alternatively, or in addition, compounds provided herein may be administered to a patient to prevent infection in a healthy patient. Patients include humans, domesticated companion animals (pets, e.g., dogs) and livestock animals. A method for treating a disorder may comprise administering to a patient in need of treatment a therapeutically effective amount of the pharmaceutical composition.

Pharmaceutical compositions may be packaged or used for the manufacture of a medicament for treatment. Packaged pharmaceutical preparations include a container holding a therapeutically effective amount of Sovaprevir and may further include labeling (e.g., instructions) indicating that the contained composition is to be used for treating the disorder.

EXAMPLES

Sovaprevir was prepared according to the syntheses in U.S. Pat. No. 7,906,619, the content of which in its entirety is herein incorporated by reference.

Example 1

Form A

A mixture of primarily Form A and a lesser amount of Form B resulted directly from the synthesis of Sovaprevir. Recrystallizing from isopropanol provided a mixture of primarily Form A and a lesser amount of Form B.

FIG. 1 shows the results of XRPD analysis of Form A.

Figure 2:
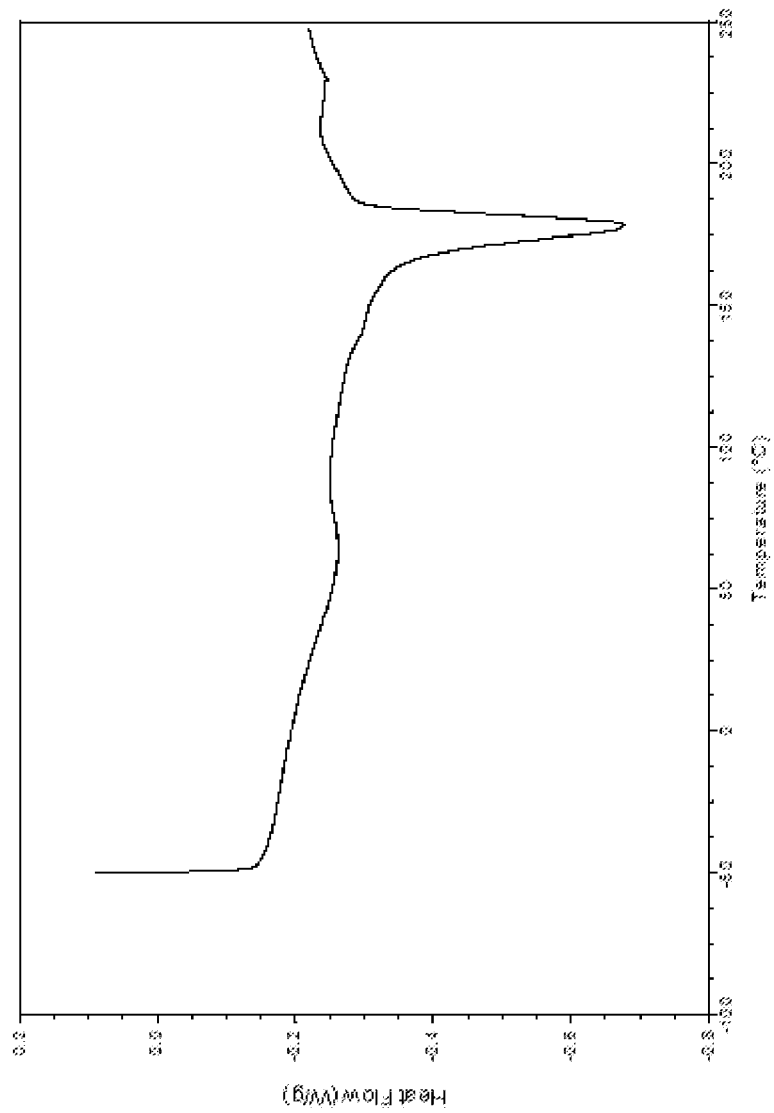
FIG. 2 is a graph of heat flow (Watts per gram, W/g) versus temperature (° C.) showing the results of differential scanning calorimetry analysis of the Form A polymorph of Example 1.

FIG. 2 shows the results of DSC analysis. A broad endotherm was present at 63° C., a shoulder was present at 143° C., and a primary endotherm was present at 179° C.

Figure 3:
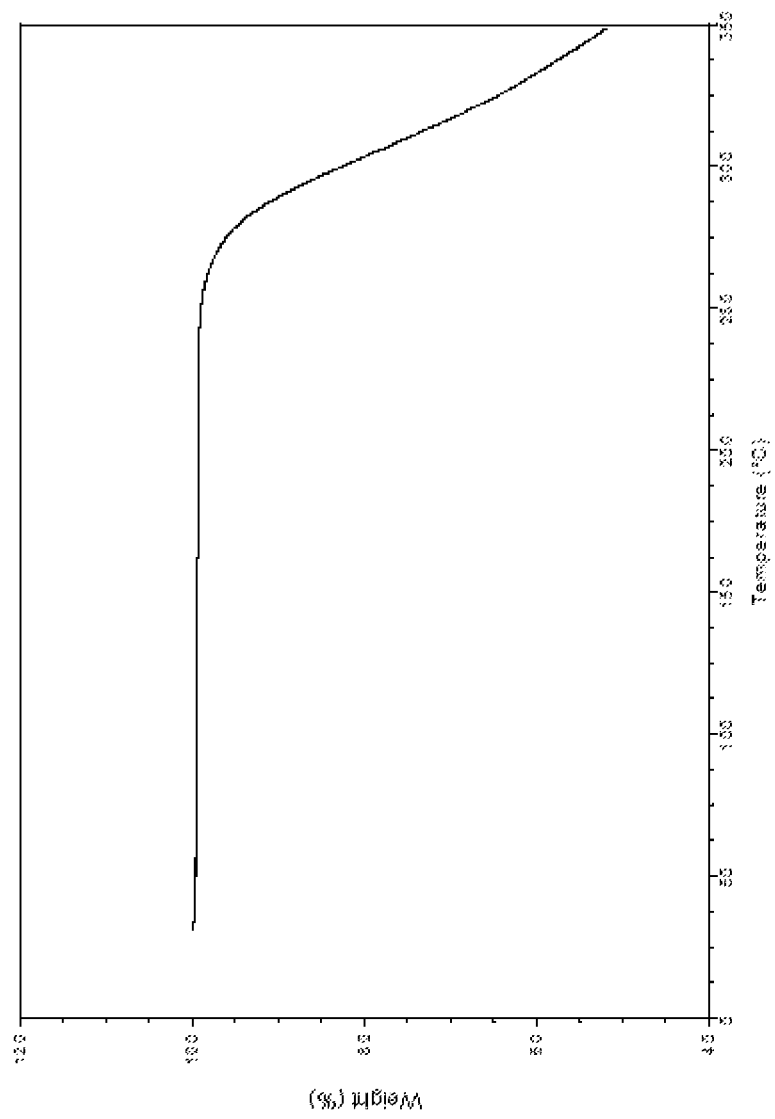
FIG. 3 is a graph of weight (percent) versus temperature (° C.) showing the results of thermogravimetric analysis of the Form A polymorph of Example 1.

FIG. 3 shows the results of TGA analysis. Weight loss below 150° C. was 0.56%.

Analysis by Karl Fisher determined that the polymorph of Example 1 contained 0.48 wt % (0.021 moles per mole Sovaprevir) water.

Analysis by variable temperature XRPD found peaks assigned to Form A were present up to 150° C. At and above 200° C. the sample was amorphous.

Example 2

Form B

Form B resulted from a slow evaporation experiment in acetonitrile:water 80:20 (v/v), and was successfully reproduced on a larger scale twice. Solutions of Sovaprevir were prepared in acetonitrile:water 80:20 (v/v) in which the Sovaprevir was sonicated between aliquot additions. Once a mixture reached complete dissolution, as judged by visual observation, the solution was filtered through a 0.2-μm nylon filter. In some cases, aliquots of antisolvent were added with stirring. The solution was allowed to evaporate from a vial covered with aluminum foil perforated with pinholes. Solutions were allowed to evaporate to dryness unless designated as partial slow evaporations. The solids were isolated and analyzed.

FIG. 4 shows the results of XRPD analysis.

Figure 5:
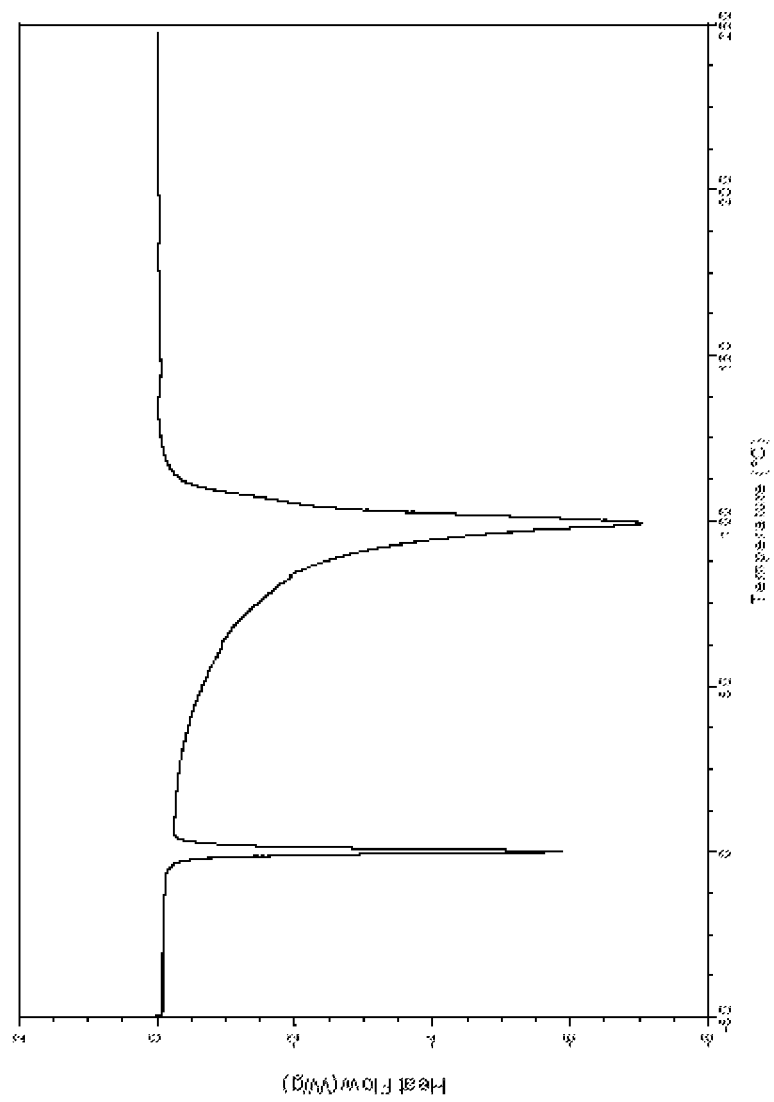
FIG. 5 is a graph of heat flow (Watts per gram, W/g) versus temperature (° C.) showing the results of differential scanning calorimetry analysis of the Form B polymorph of Example 2.

FIG. 5 shows the results of DSC analysis. A sharp endotherm (87 J/g) was observed at 0° C., and a broader primary endotherm was observed at 99° C.

Figure 6:
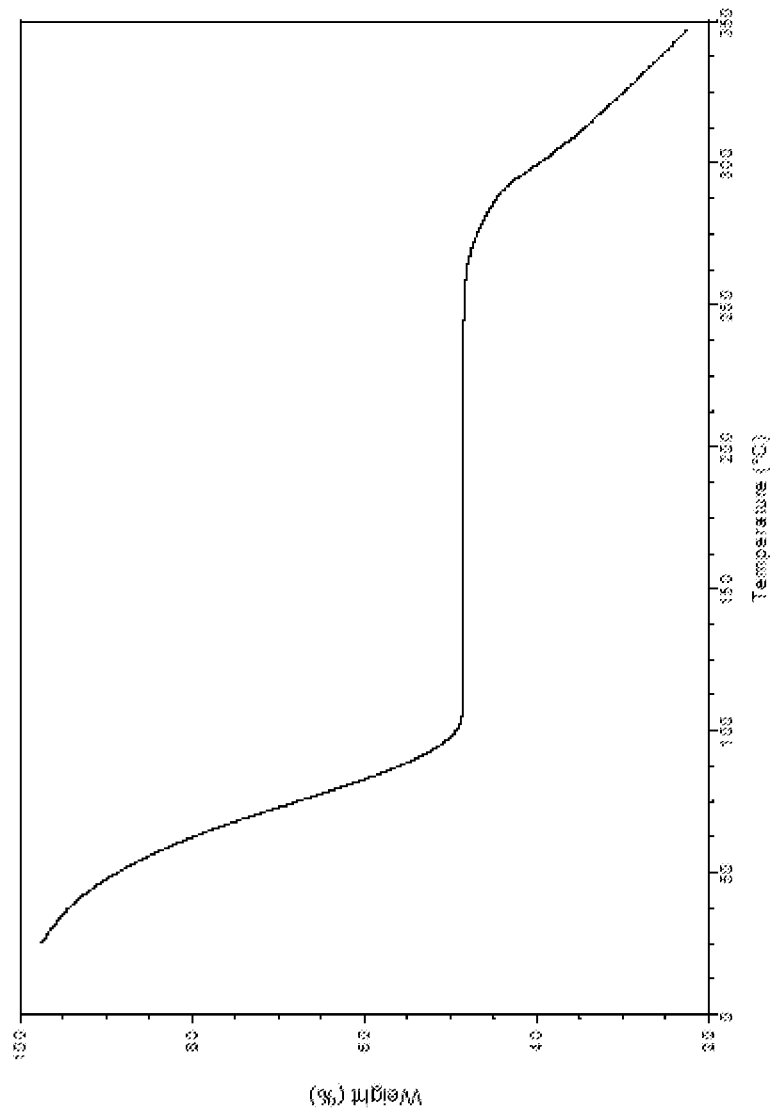
FIG. 6 is a graph of weight (percent) versus temperature (° C.) showing the results of thermogravimetric analysis of the Form B polymorph of Example 2.

FIG. 6 shows the results of TGA analysis. Weight loss of 49% occurred between 25 and 140° C.

Analysis by variable temperature XRPD found peaks assigned to Form B were present up to 75° C. At and above 125° C. the sample was amorphous.

Example 3

Form C

Form C resulted from a slurry experiment at approximately 48° C. in isopropanol and was successfully reproduced on a larger scale multiple times at both ambient and elevated temperatures.

Solutions of Sovaprevir were prepared by adding enough solids to isopropanol at ambient conditions so that undissolved solids were present. The mixture was then loaded onto an orbit shaker in a sealed vial at ambient or elevated temperature for an extended period of time, typically approximately 1 week. The solids were isolated by vacuum filtration or by withdrawing solvent via pipette and allowing the solids to air dry at ambient conditions prior to analysis. In some cases, portions of slurries were packed into 1.0 mm glass capillaries and analyzed by XRPD as suspensions.

FIG. 7 shows the results of XRPD analysis. Analysis by variable temperature XRPD found peaks assigned to Form C were present up to 150° C. At and above 200° C. the sample was amorphous.

Figure 8:
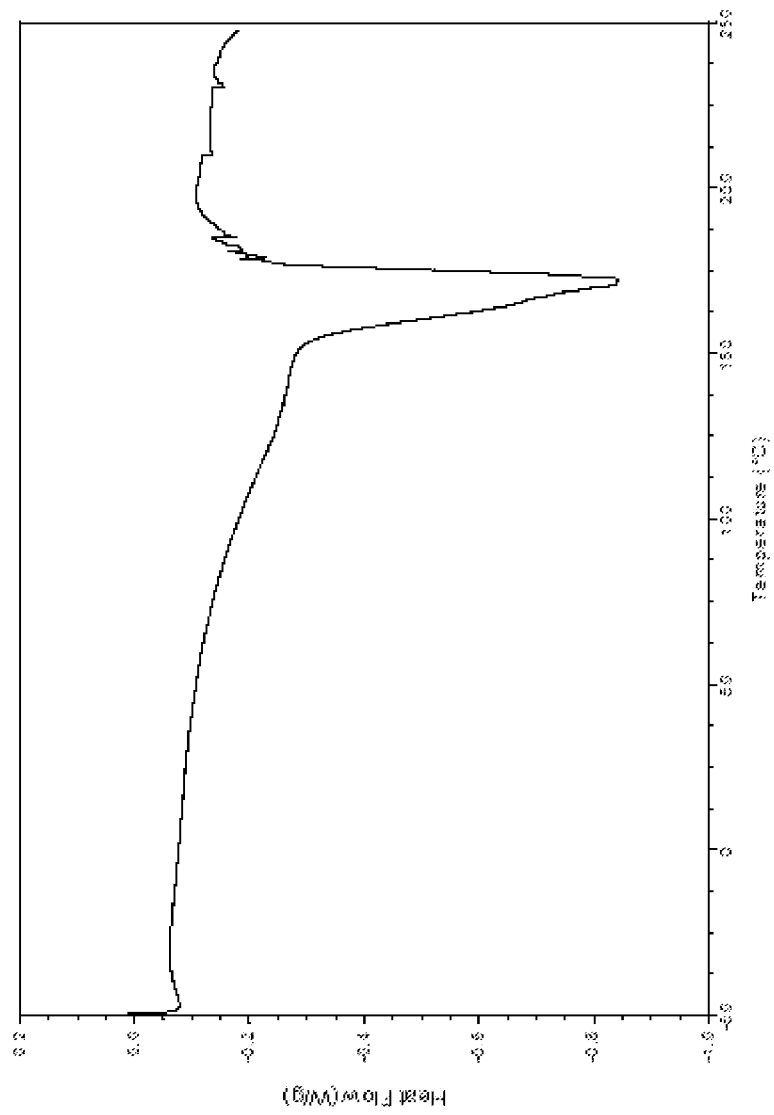
FIG. 8 is a graph of heat flow (Watts per gram, W/g) versus temperature (° C.) showing the results of differential scanning calorimetry analysis of the Form C polymorph of Example 3.

FIG. 8 shows the results of DSC analysis. A broad endotherm was observed at 172° C.

Figure 9:
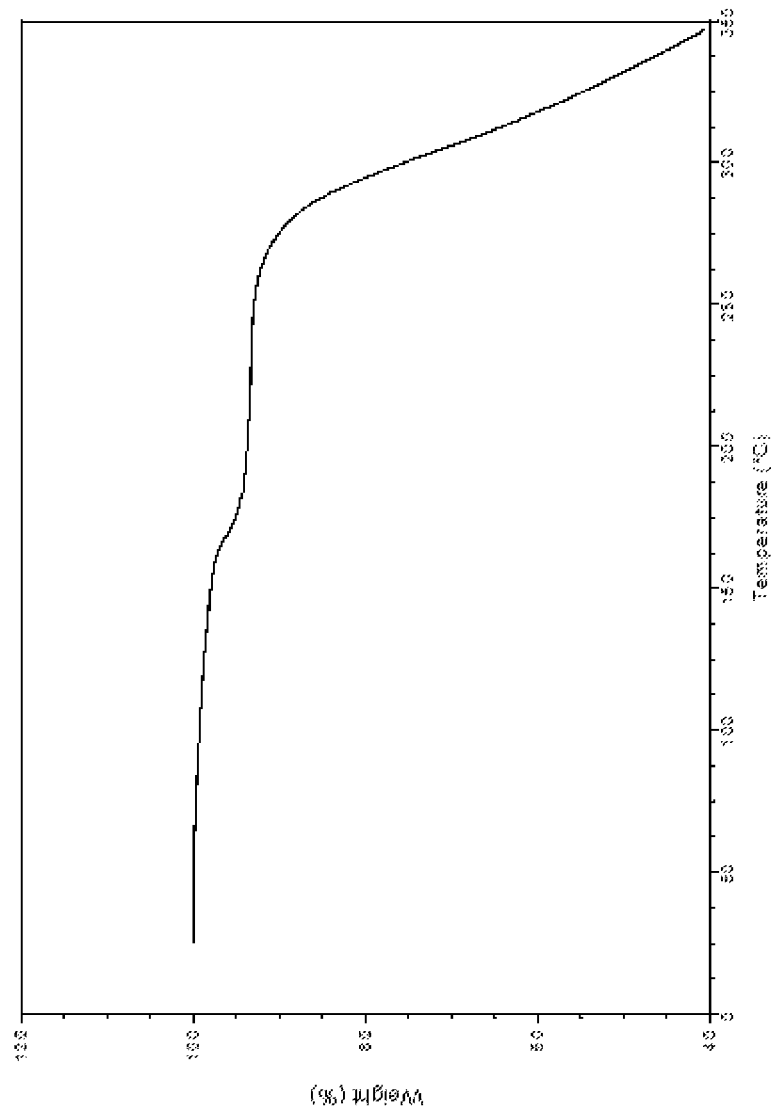
FIG. 9 is a graph of weight (percent) versus temperature (° C.) showing the results of thermogravimetric analysis of the Form C polymorph of Example 3.

FIG. 9 shows the results of TGA analysis. Weight loss of 2% occurred between 25 and 150° C. Weight loss of 5.5% occurred between 150 and 260° C.

Example 4

Form D

Form D resulted from crystallization from ethyl acetate:heptane 1:1 (v/v). FIG. 10 shows the results of XRPD analysis. Analysis by variable temperature XRPD found peaks assigned to Form D were present up to 180° C. At and above 230° C. the sample was amorphous.

Figure 11:
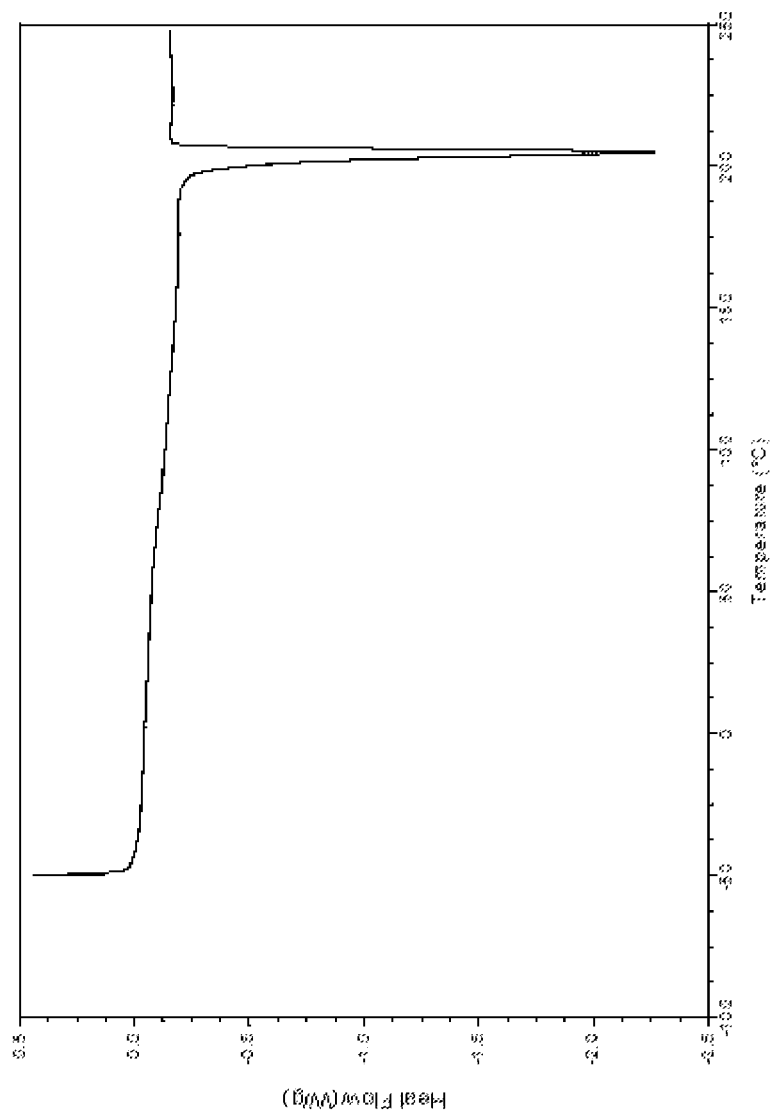
FIG. 11 is a graph of heat flow (Watts per gram, W/g) versus temperature (° C.) showing the results of differential scanning calorimetry analysis of the Form D polymorph of Example 4.

FIG. 11 shows the results of DSC analysis. A primary endotherm was at 205° C.

Figure 12:
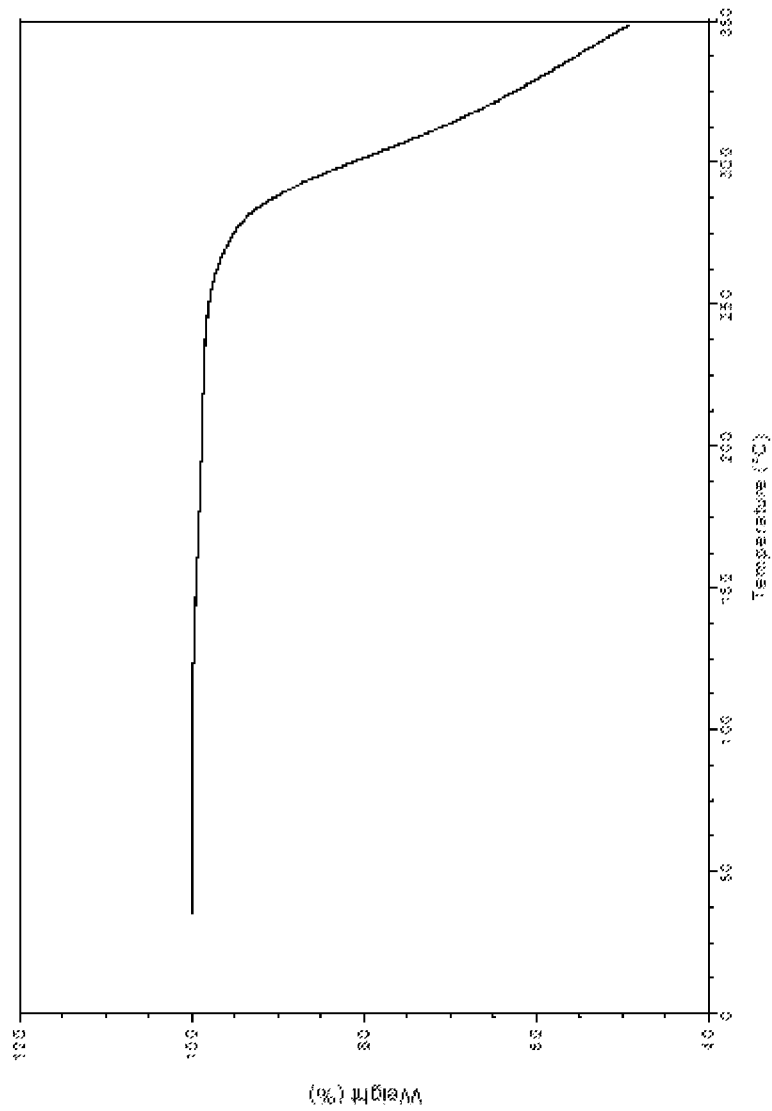
FIG. 12 is a graph of weight (percent) versus temperature (° C.) showing the results of thermogravimetric analysis of the Form D polymorph of Example 4.

FIG. 12 shows the results of TGA analysis. A weight loss of 0.865 occurred between 30 and 180° C.

Example 5

Form E

Form E resulted directly from the synthesis of Sovaprevir. Form E is crystallized by refluxing in isopropanol with 1% $H_2O$. It is believed that Form E is a isopropanol solvate.

FIG. 13 shows the results of XRPD analysis. In an embodiment the Form E polymorph exhibits an X-ray powder diffraction pattern that substantially corresponds to the X-ray powder diffraction pattern shown in FIG. 13.

Figure 14:
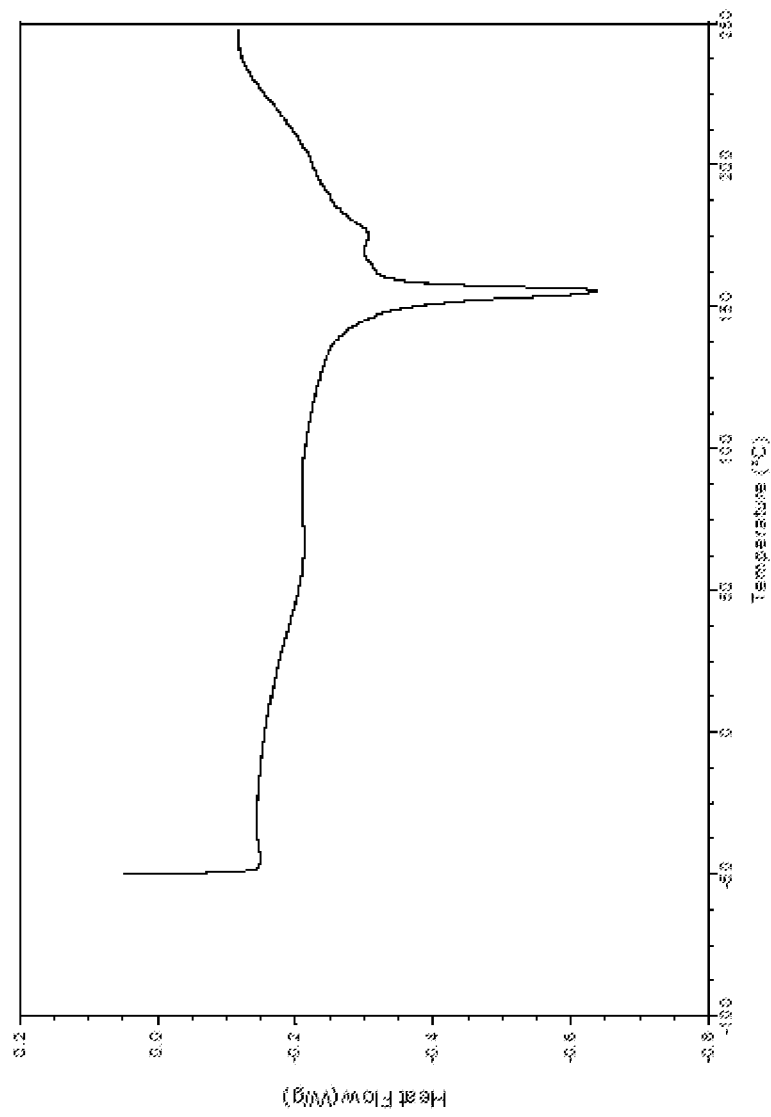
FIG. 14 is a graph of heat flow (Watts per gram, W/g) versus temperature (° C.) showing the results of differential scanning calorimetry analysis of the Form E polymorph of Example 5.

FIG. 14 shows the results of DSC analysis. A primary endotherm was at 156° C.

Figure 15:
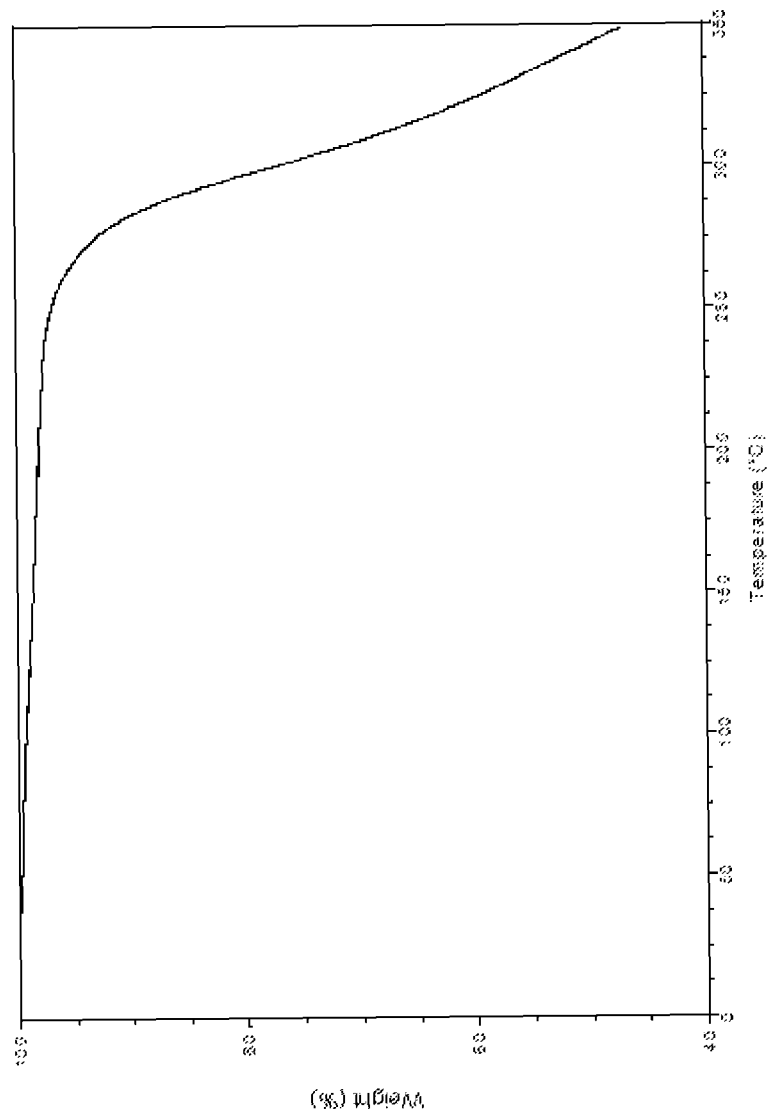
FIG. 15 is a graph of weight (percent) versus temperature (° C.) showing the results of thermogravimetric analysis of the Form E polymorph of Example 5.

FIG. 15 shows the results of TGA analysis. Weight loss of 1.2% occurred between 30 and 140° C.

Analysis by variable temperature XRPD found peaks assigned to Form E were present up to 125° C. At and above 175° C. the sample was amorphous.

Karl Fischer analysis determined that 0.28 wt % (0.12 moles per mole Sovaprevir) water was present.

Instrumental Techniques
X-Ray Powder Diffraction (XPRD)
Intel XRG-3000 Diffractometer XRPD patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 µm, and the samples were analyzed for 5 minutes.

Shimadzu XRD-6000 Diffractometer

XRPD patterns were collected using a Shimadzu XRD-6000 X-ray powder diffractometer. An incident beam of Cu Kα radiation was produced using a long, fine-focus X-ray tube (40 kV, 40 mA) and a curved graphite monochromator. The divergence and scattering slits were set at 1°, and the receiving slit was set at 0.15 mm. Diffracted radiation was detected by a NaI scintillation detector. Data were collected and analyzed using XRD-6100/7000 software (v. 5.0). Prior to the analysis, a silicon standard (NIST SRM 640c) was analyzed to verify the Si 111 peak position. Samples were prepared for analysis by placing them in an aluminum holder with a silicon zero-background insert. Patterns were collected using a 0-2θ continuous scan at 3°/min. (0.4 sec/0.02° step) from 2.5 to 40° 2θ.

Shimadzu XRD-6000 Diffractometer (Variable Temperature)

Variable-temperature XRPD patterns (VT-XRPD) were collected using a Shimadzu XRD-6000 X-ray powder diffractometer equipped with an Anton Paar HTK 1200 high-temperature stage. Prior to the analysis, a silicon standard (NIST SRM 640c) was analyzed to verify the Si 111 peak position, and vanillin and sulfapyridine standards were analysed to verify the stage temperature. The sample was packed in a ceramic holder and analyzed from 2.5 to 40° 2θ at 3°/min (0.4 sec/0.02° step). The heating rate was 10° C./min.

Differential Scanning Calorimetry (DSC)

Differential scanning calorimetry (DSC) was performed using a TA Instruments differential scanning calorimeter Q2000. The sample was placed into an aluminum DSC pan, and the weight accurately recorded. The pan was covered with a lid and then crimped. The sample cell was equilibrated at −50° C. (or 25° C., depending on the sample) and heated under a nitrogen purge at a rate of 10° C./min, up to a final temperature of 250° C. Indium metal was used as the calibration standard. Reported temperatures are at the transition maxima.

Thermogravimetry (TGA)

Thermogravimetric (TGA) analyses were performed using a TA Instruments 2950 thermogravimetric analyzer. Each sample was placed in an aluminum sample pan and inserted into the TGA furnace. The furnace was heated under nitrogen at a rate of 10° C./min, up to a final temperature of 350° C. Nickel and Alumel™ were used as the calibration standards.

Karl Fischer Titration Analysis (KF)

Coulometric Karl Fischer (KF) analysis for water determination was performed using a Mettler Toledo DL39 KF titrator. A blank titration was carried out prior to analysis. The sample was prepared under a dry nitrogen atmosphere or at ambient conditions when ambient relative humidity <5%, where approximately 10-20 mg of the sample were dissolved in approximately 1 mL dry Hydranal—Coulomat AD in a vial (in some cases, vials were pre-dried). The entire solution was added to the KF coulometer through a septum and mixed for 10 seconds. The sample was then titrated by means of a generator electrode, which produces iodine by electrochemical oxidation: 2 I$^-$→I$_2$+2e$^-$. Two or three replicates were obtained to ensure reproducibility.

What is claimed is:

1. A crystalline form of Sovaprevir comprising polymorph E.

2. The crystalline Sovaprevir form of claim 1 wherein Polymorph E exhibits an X-ray powder diffraction pattern having the characteristic 2θ values of FIG. 13.

3. A Crystalline polymorph Form E of Sovaprevir, wherein polymorph Form E is characterized by an X-ray powder diffraction pattern obtained from a Cu Kα source which comprises peaks at 2θ values of
4.5±0.2, 10.9±0.2, 17.4±0.2, 20.2±0.2, and 21.7±0.2; or
9.0±0.2, 12.3±0.2, 18.6±0.2, 20.7±0.2, and 22.2±0.2; or
9.7±0.2, 13.7±0.2, 19.4±0.2, and 21.3±0.2.

4. The crystalline Sovaprevir form of claim 1, wherein polymorph E has a primary endotherm at 156° C. as determined by DSC.

5. A composition comprising a crystalline form of Sovaprevir wherein at least 90 wt % of the Sovaprevir is the Form E polymorph.

6. The composition of claim 5, wherein the composition comprises less than about 10 wt % of a Form D polymorph.

7. A pharmaceutical composition comprising crystalline polymorph form E of Sovaprevir according to claim 3, in combination with a physiologically acceptable carrier or excipient.

8. A pharmaceutical composition according to claim 7 wherein the composition is a tablet or a capsule.

9. A method for treating HCV, comprising administering to a patient in need of such treatment a therapeutically effective amount of a pharmaceutical composition according to claim 8.

10. A method according to claim 9, wherein the patient is a human.

11. A method according to claim 9, wherein the pharmaceutical composition is administered orally.

12. The crystalline Sovaprevir form of claim 1, wherein polymorph E has a primary endotherm at about 151° C. to about 161° C. as determined by DSC.

13. The crystalline Sovaprevir form of claim 3, wherein polymorph E is characterized by an X-ray powder diffraction pattern obtained from a Cu Kα source which comprises peaks at 2θ values of 4.5±0.2, 10.9±0.2, 17.4±0.2, 20.2±0.2, and 21.7±0.2.

14. The crystalline Sovaprevir form of claim 3, wherein polymorph E is characterized by an X-ray powder diffraction pattern obtained from a Cu Kα source which comprises peaks at 2θ values of 9.0±0.2, 12.3±0.2, 18.6±0.2, 20.7±0.2, and 22.2±0.2.

15. The crystalline Sovaprevir form of claim 3, wherein polymorph E is characterized by an X-ray powder diffraction pattern obtained from a Cu Kα source which comprises peaks at 2θ values of 9.7±0.2, 13.7±0.2, 19.4±0.2, and 21.3±0.2.

16. A crystalline polymorph Form E of Sovaprevir, wherein polymorph Form E is characterized by an X-ray powder diffraction pattern obtained from a Cu Kα source which comprises peaks at 2θ values of:

4.5±0.2, 9.0±0.2, 9.7±0.2, 10.9±0.2, 12.3±0.2, 13.7±0.2, 17.4±0.2, 18.6±0.2, 19.4±0.2, 20.2±0.2, 20.7±0.2, 21.7±0.2, 21.3±0.2, and 22.2±0.2.

17. A crystalline polymorph Form E, of Sovaprevir that exhibits an X-ray powder diffraction pattern obtained from a Cu Kα source that substantially corresponds to the X-ray powder diffraction pattern shown in FIG. 13.

* * * * *